(12) United States Patent
Weiss et al.

(10) Patent No.: US 12,027,263 B2
(45) Date of Patent: Jul. 2, 2024

(54) WIRELESS DIGITAL TREATMENT AND WARNING SYSTEM AND DISPLAY FOR VETERINARIAN ANIMAL CAGES

(71) Applicants: Mitchell Weiss, Los Angeles, CA (US); Thomas Wang, Alhambra, CA (US); William F. Ryczek, La Verne, CA (US)

(72) Inventors: Mitchell Weiss, Los Angeles, CA (US); Thomas Wang, Alhambra, CA (US); William F. Ryczek, La Verne, CA (US)

(73) Assignee: Mitchell Weiss, Los Angeles, CA (US)

( * ) Notice: Subject to any disclaimer, the term of this patent is extended or adjusted under 35 U.S.C. 154(b) by 30 days.

(21) Appl. No.: 17/544,317

(22) Filed: Dec. 7, 2021

(65) Prior Publication Data

US 2022/0181014 A1  Jun. 9, 2022

Related U.S. Application Data

(60) Provisional application No. 63/122,786, filed on Dec. 8, 2020.

(51) Int. Cl.
*G16H 40/63* (2018.01)
*A01K 1/03* (2006.01)
*G08B 5/36* (2006.01)

(52) U.S. Cl.
CPC ............. *G16H 40/63* (2018.01); *A01K 1/031* (2013.01); *G08B 5/36* (2013.01)

(58) Field of Classification Search
CPC ........... G16H 40/63; A01K 1/031; G08B 5/36
See application file for complete search history.

(56) References Cited

U.S. PATENT DOCUMENTS 6,397,190 B1 * 5/2002 Goetz .................. G06F 15/025
                                                       235/375
9,210,755 B2 * 12/2015 Grajcar ................. A01K 45/00
(Continued)

FOREIGN PATENT DOCUMENTS

CN       206878872 U  *  1/2018  ............. H04L 29/08
CN       207948505 U  * 10/2018  ............... A01K 1/03
WO   WO-2020073060 A1 *  4/2020  ........... A61B 5/0002

OTHER PUBLICATIONS

Machine translation of CN-206878872-U, Chen C, Jan. 2018 (Year: 2018).*

(Continued)

*Primary Examiner* — Tien Q Dinh
*Assistant Examiner* — Katherine June Bolek
(74) *Attorney, Agent, or Firm* — Eric Karich; Karich & Associates

(57) ABSTRACT

A wireless digital treatment and warning system for veterinarian animal cages includes software that reads stored data for a course of treatment and prescription medication information for a particular animal in a particular cage, identifies the unique veterinarian animal cage number for the particular animal, identifies a digital display panel number paired with the unique veterinarian animal cage number for the particular animal, visually outputs digitized treatment information for the particular animal in time-synchronized accordance with the course of treatment and prescription medication information for the particular animal, and triggers the colored warning lights to activate as a visual warning alert to feed, medicate, or take care of the particular animal.

8 Claims, 7 Drawing Sheets

(56) References Cited

U.S. PATENT DOCUMENTS

2004/0217858 A1* 11/2004 Ingley, III .............. A01K 1/031
　　　　　　　　　　　　　　　　　　　　　　340/573.1
2012/0085291 A1* 4/2012 Conger ................ A01K 1/0047
　　　　　　　　　　　　　　　　　　　　　　119/419

OTHER PUBLICATIONS

Machine translation of CN-207948505-U, Chen A, Oct. 2018 (Year: 2018).*

* cited by examiner

WIRELESS DIGITAL TREATMENT AND WARNING SYSTEM AND DISPLAY FOR VETERINARIAN ANIMAL CAGES

CROSS-REFERENCE TO RELATED APPLICATIONS

This application for a utility patent claims the benefit of U.S. Provisional Application No. 63/122,786, filed Dec. 8, 2020.

BACKGROUND

Embodiments of the invention described in this specification relate generally to veterinarian systems for treatment and care of animals, and more particularly, to a wireless digital treatment and warning system and display for veterinarian animal cages.

Presently, veterinarian offices use informal means of communication with staff regarding the course of treatment for animals under the care of a veterinarian doctor. Typical veterinarian animal treatment/care protocols include handwritten notes that are delivered to the staff members, or simply left on or near a cage of an animal. Course of treatment is stored in computers that are separate from the cage, not on the cage itself. The system is prone to error since errors can occur when writing out the instructions on paper from the digitally stored, computer-based course of treatment that is approved by the veterinarian. In addition, paper-based notes and instructions can be damaged, obscured, lost, or otherwise rendered difficult or impossible to follow. Furthermore, a staff member may not know of a note left from a prior staff member, and may not notice it in time.

There are no existing devices or systems that provide cage-specific instant access to course of treatment, medications, and notes stored in a computer system by the veterinarian doctor for care of the animal in the cage. There also is not existing option to determine vital signs of animals in cages at an instant, or to visually alert a staff member, e.g., with a bright or blinking light, about important information, such as an aggressive animal, or a stoppage on their eating prior to surgery.

Therefore, what is a long-felt need in the field for a better way to provide instruction for the care and treatment of animals in veterinarian animal cages.

SUMMARY OF THE INVENTION

The present invention teaches certain benefits in construction and use which give rise to the objectives described below.

The present invention provides a wireless digital treatment and warning system for displaying information about an animal in a veterinarian animal cage. The system includes a veterinarian animal cage, and a digital display panel that is physically associated with the veterinarian animal cage. The digital display panel has a wireless data communication device, and at least one display screen unit disposed on the digital display panel. A computer device is operably connected with the at least one display screen unit for visually outputting information related to the animal and a course of treatment for the animal housed in the veterinarian animal cage.

A primary objective of the present invention is to provide a wireless digital treatment and warning system having advantages not taught by the prior art.

Another objective is to provide a wireless digital treatment and warning system that enables a veterinarian or other caregiver to update information about an animal in a specific cage, including information about medications, course of treatment, and other information useful in caring for and treating an animal.

A further objective is to provide a wireless digital treatment and warning system that provides treatment information that can be updated in real time.

A further objective is to provide a wireless digital treatment and warning system that proactively provides warnings to caregivers to ensure that care is correctly provided in a safe manner for both the animal and caregiver.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention.

DETAILED DESCRIPTION OF THE INVENTION

Figure 1:
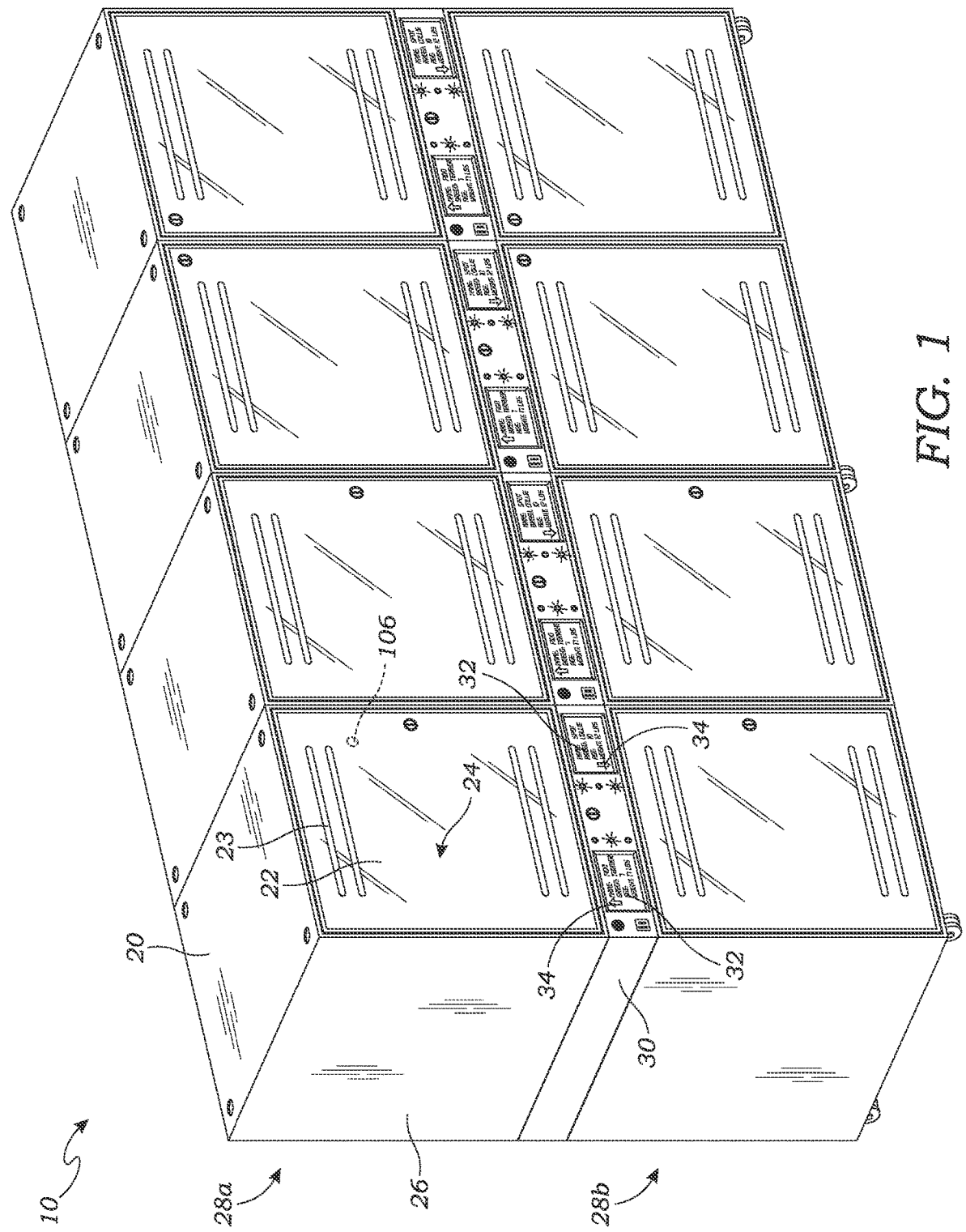
FIG. 1 is a perspective view of a first embodiment of a wireless digital treatment and warning system.

A wireless digital treatment and warning system 10 for veterinarian animal cages 20. The wireless digital treatment and warning system 10 includes a digital display panel 30 along which one or more display screens 32 are disposed, for displaying information pertaining to an animal being housed in the cage 20, as discussed in greater detail below.

FIG. 1 is a perspective view of a first embodiment of a wireless digital treatment and warning system 10, according to the present invention. As shown in FIG. 1, the animal cages 20 may be of generally standard construction, having a front hinged door 22 for access to an internal chamber 24 defined by a cage body 26. The front hinged door 22 may include ventilation holes 23, slots, or similar features well known in the art. Since the general construction of such cages are well known in the art, they are not described in greater detail herein.

In this embodiment, there are four top cages 28A mounted atop four bottom cages 28B, with a digital display panel 30 mounted therebetween. The digital display panel 30 is positioned so that each of the display screens 32 is associated with one of the cages. In this case, with one cage on top, one cage on the bottom, and the panel in between, one of the panels is associated with the top cage, and the other is associated with the bottom cage. A visual indicator, such as an arrow 34, may be displayed on the screens 32, to indicate the cage associated with the screen. Alternatively, the arrow 32 could also be printed adjacent the screen 32, or other forms of indicators may be used, including displays on the screen 32, the physical location of the screen 32, etc.

Furthermore, other arrangements of screens 32 and cages 20 may be used, so long as a user can determine the association. A single cage and a single screen may be used together, and/or any other arrangement, some of which are discussed in greater detail below.

In some embodiments, the digital display panel 30 further includes a plurality of colored warning lights 36. The digital display panel 30 includes a computing device, shown in FIG. 8 and discussed below, which includes software that receives, stores, and displays information about the animal, including identification information (e.g., name, age, owner, etc.), information about a course of treatment and prescription medication information for each animal undergoing treatment. In some embodiments, the software associates a unique veterinarian animal cage number 38 (shown in FIG. 5) with the stored data for the course of treatment and prescription medication information for a particular animal in the animal cage, along with other suitable information (e.g., owner name and contact information, associated veterinarian, medical history, etc.).

In some embodiments, the software reads the stored data for the course of treatment and prescription medication information for the particular animal in the veterinarian animal cage, identifies the unique veterinarian animal cage number for the particular animal, identifies the digital display panel number paired with the unique veterinarian animal cage number for the particular animal, visually outputs digitized treatment information for the particular animal in time-synchronized accordance with the course of treatment and prescription medication information for the particular animal, and triggers one or more of the colored warning lights 36 as a visual warning alert that it is presently time to medicate, time to feed, or not medicate/feed when an animal is aggressive. In this embodiment, the colored warning lights 36 include a medicate light 40 to indicate when medication should be administered, and an aggressive warning light 42 to indicate if the animal is aggressive, and special care must be taken. The colored warning lights 36 may further include a check vitals light 44 that alerts the caregiver to check the animal's vitals, and/or take any other actions that may be required.

These lights 38 may be separate lights (e.g., LEDs) as illustrated, or they may be displayed on the display panel 30. The number of lights, how they are displayed, and other factors may be varied by one skilled in the art without departing from the present invention, and should be considered within the scope of the claims.

Some embodiments of the invention include a wireless digital treatment and warning system 10 for veterinarian animal cages. In some embodiments, the wireless digital treatment and warning system includes a steel digital display panel 30 along which one or more display screens are disposed. In some embodiments, a size of the steel digital display panel is approximately seven vertical inches by thirty horizontal inches. In some other embodiments, the size of the steel digital display panel 30 is approximately seven horizontal inches by thirty vertical inches. In some embodiments, the digital display panel 30 includes a plurality of colored warning lights. In some embodiments, the digital display panel 30 is mounted to a veterinarian animal cage. In some embodiments, the digital display panel 30 is mounted to the side of the cage. In some embodiments, the digital display panel 30 is mounted to the bottom of the cage. In some embodiments, multiple veterinarian animal cages are stacked on top of the digital display panel 30, which is mounted to the bottom of the bottom cage. In some embodiments, the digital display panel 30 is mounted vertically to multiple veterinarian animal cages that are stacked on top each other. In some embodiments, the digital display panel 30 is wirelessly connected to a computing device of the wireless digital treatment and warning system. In some embodiments, the computing device includes software that stores course of treatment and prescription medication information for each animal undergoing a course of treatment by a veterinarian doctor. In some embodiments, the software associates a unique veterinarian animal cage number with the stored data for the course of treatment and prescription medication information for a particular animal in the veterinarian animal cage. In embodiments, the software pairs a digital display panel 30 number with each unique veterinarian animal cage number.

In some embodiments, the software reads the stored data for the course of treatment and prescription medication information for the particular animal in the veterinarian animal cage, identifies the unique veterinarian animal cage number for the particular animal, identifies the digital display panel 30 number paired with the unique veterinarian animal cage number for the particular animal, visually outputs digitized treatment information for the particular animal in time-synchronized accordance with the course of treatment and prescription medication information for the particular animal, and triggers one or more of the colored warning lights to activate as a visual warning alert that it is presently time to medicate, time to feed, or not medicate/feed when an animal is aggressive.

Embodiments of the wireless digital treatment and warning system 10 for veterinarian animal cages described in this specification differ from and improve upon currently existing options. In particular, some embodiments differ existing course of treatment practices for animals in veterinarian animal cages, which typically include hand-written notes or other informal information relay. While course of treatment and medication information is normally stored digitally in a computing device by veterinarians, there is no existing system that ties together the digital information with the cages to be used as instruction for feeding and/or medicating. Furthermore, none of the existing veterinarian animal cages incorporated display panels or warning lights that can provide visual reminders to feed or medicate an animal in the cage.

In addition, some embodiments of the wireless digital treatment and warning system 10 for veterinarian animal cages improve upon the currently existing options by providing a display system that presents the relevant treatment and animal care information in full view of anyone nearby the cage, and because the displayed information is driven by software, the information is coordinated with the course of treatment from the doctor. This is a vast improvement over existing veterinarian animal cage systems and treatment/care protocols which typically involve too much time to retrieve the information when it can be right there with the animal in question. The result is less confusion and less room for error in treatment.

The wireless digital treatment and warning system 10 for veterinarian animal cages of the present disclosure may be comprised of the following elements. This list of possible constituent elements is intended to be exemplary only and it is not intended that this list be used to limit the wireless digital treatment and warning system 10 for veterinarian animal cages of the present application to just these elements. Persons having ordinary skill in the art relevant to the present disclosure may understand there to be equivalent elements that maybe substituted within the present disclosure without changing the essential function or operation of the wireless digital treatment and warning system 10 for veterinarian animal cages.

1. Digital display panel 30 mounted to or otherwise associated with the cage 20.
2. One or more display screens 32 disposed on the digital display panel 30.
3. The display panel 30 may further include colored warning lights 36 disposed on the digital display panel 30.
4. Software that runs on a computing device of the wireless digital treatment and warning system and that stores course of treatment and medication data for each animal in a separate veterinarian cage
5. Wireless communication devices at the computing device and the digital display panel 30 for wireless data transmission of warnings to feed or mediate (light up the warning lights) and display course of treatment information (e.g., 5 grams of food for animal in cage every four hours, one dose of medication X at noon for animal in cage).

The various elements of the wireless digital treatment and warning system 10 for veterinarian animal cages of the present disclosure include three basic components: (i) the digital display panel 30 along which the screens and warning lights are disposed for visual inspection (can be a steel panel, but not required to be steel), (ii) the colored warning lights (either still or flashing), and (iii) the display screen(s) (typically at least two display screens, one for static information like name and age of animal, and the other one for treatment information, like medicine Rx every four hours as prescribed by Dr. I. Care, but two screens are not required . . . some deployments work with one screen, other deployments have more than two screens).

The wireless digital treatment and warning system 10 for the animal cages 20 of the present disclosure generally works by visually outputting a single course of treatment for the one animal occupying the cage, along with warning lights 36 that are triggered in time-synchronization with expressed timing of veterinarian directed feeding times or medication administration times, along with any other relevant information (e.g., change bandages daily). This assures that nothing will be missed by the veterinarian staff—feeding, medication, change of bandages, etc., are all digitally displayed and tied to the warning lights (which can statically shine when triggered, or can be configured to flash when triggered) until the procedure is accomplished and reset.

To make the wireless digital treatment and warning system 10 for veterinarian animal cages of the present disclosure, one can build the digital display panel 30 and mount the display screen(s) and warning lights, then ensure wireless device can communicate with backend computing device and software to carry out the functions of warning triggering (to feed and/or medicate a particular animal in a particular cage) in accordance with the course of treatment information and other information from the veterinarian stored digitally in the computing device. Typically, the digital display panel 30 is made from a solid material, such as steel, and similarly for the warning lights. While these components presently exist and are separately available to obtain by a person, these existing components (such as the steel digital display panel 30, the display screen unit(s), and the warning lights) are combined together in a novel way. The wireless digital treatment and warning system uses the novel combination of the components in connection with the veterinarian animal cage to provide a better way for treatment, medication administration, and monitoring of vital signs of an animal with fewer mistakes resulting in improved medical care and treatment of the animal.

Figure 2:
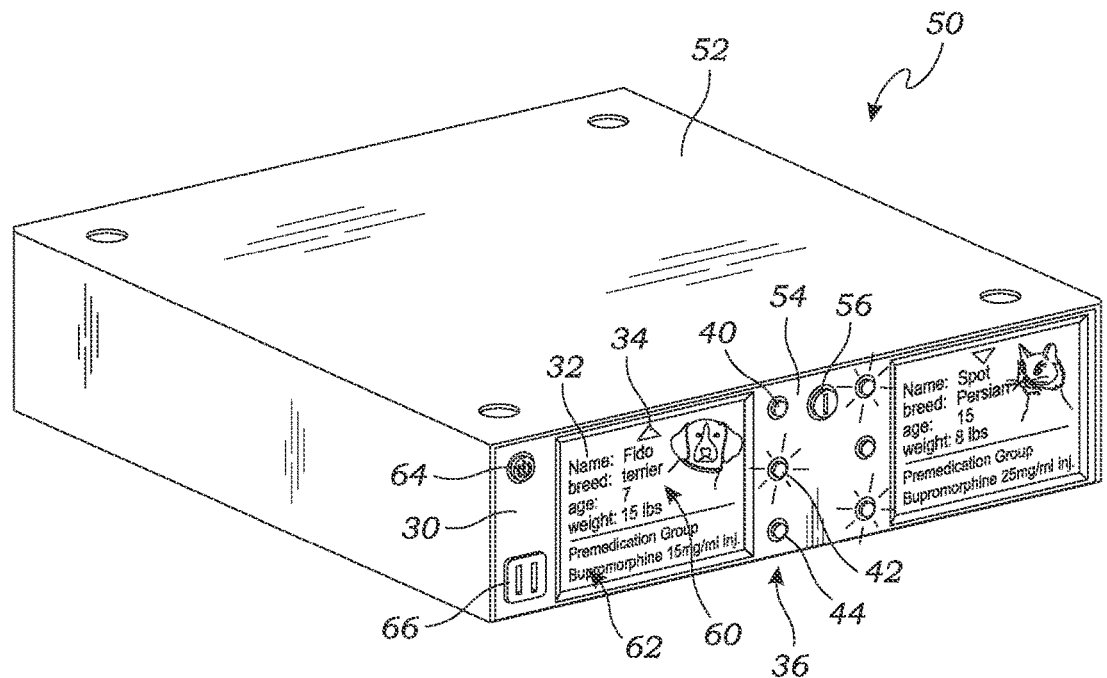
FIG. 2 is a perspective view of a second embodiment of a wireless digital treatment and warning system.
Figure 3:
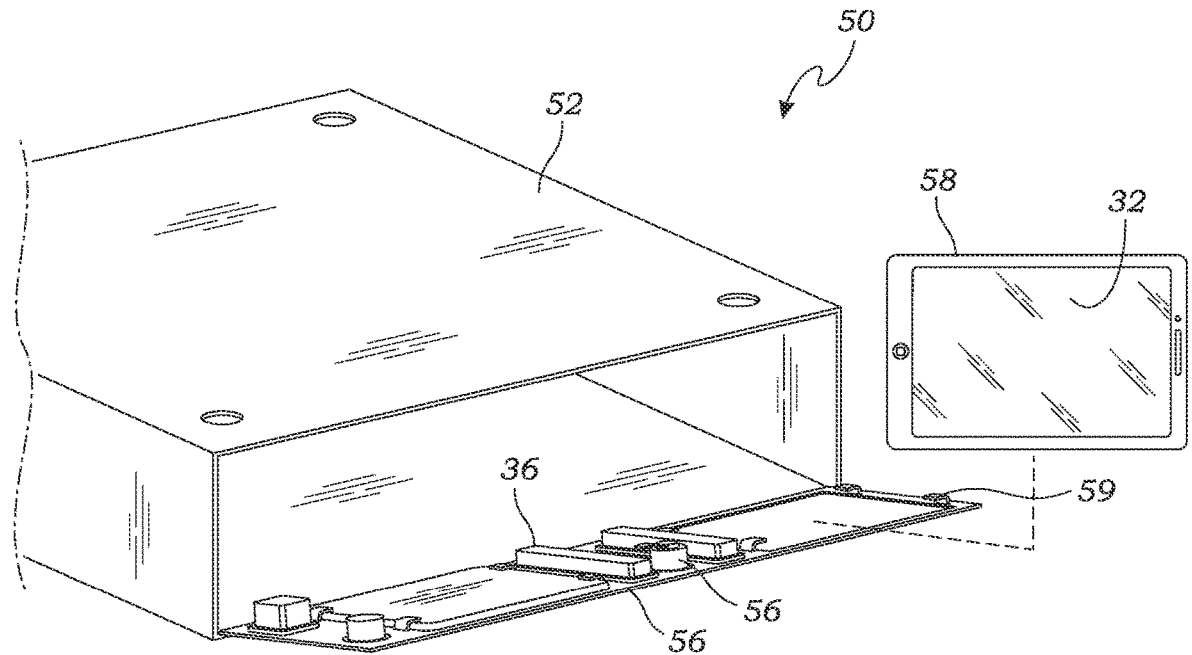
FIG. 3 is an exploded perspective view of the wireless digital treatment and warning system of FIG. 2.

FIG. 2 is a perspective view of a second embodiment of a wireless digital treatment and warning system 50. FIG. 3 is an exploded perspective view of the wireless digital treatment and warning system 50 of FIG. 2. As shown in FIGS. 2-3, the system 50 has a cuboid housing 52 that is separate from any cage, but which could be placed on, beneath, or adjacent existing cages, so that they are visually associated together in some manner determined by one skilled in the art.

As shown in FIGS. 2-3, in this embodiment, the system 50 includes a hinged front panel 54 which may secured by a latch 56 and/or lock. As shown in FIG. 3, in this embodiment the display screen 32 is provided in the form of a tablet computer 58 (e.g., an iPad) which may be engaged with a retainer mechanism 59 for securing the tablet computer 58 with the front panel 54. The tablet computer 58 may be connected to a power source (not shown), and may wirelessly communicate with any outside computers, lights, and/or other accessories.

As shown in FIG. 2, the display screen 32 displays information 60 about the animal being held in the associated cage (as shown in FIG. 1), along with treatment information 62. In this embodiment, the system 50 may further include a power switch 64 for turning the system 50 on and off, as well as a power outlet 66 which enables caregivers to plug in other electronic devices and tools for use in or adjacent the cages.

Figure 4:
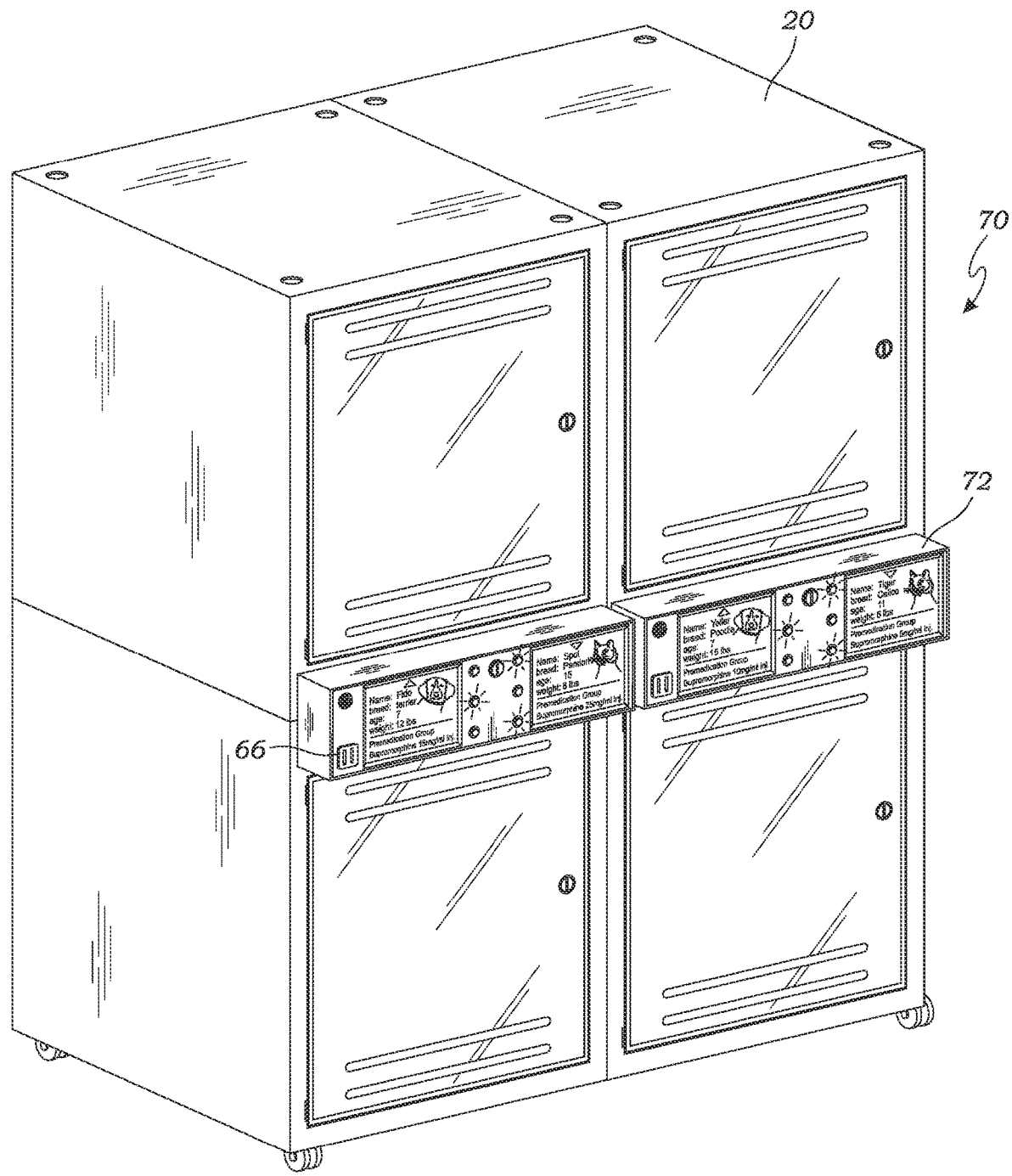
FIG. 4 is a perspective view of a third embodiment of a wireless digital treatment and warning system.
Figure 5:
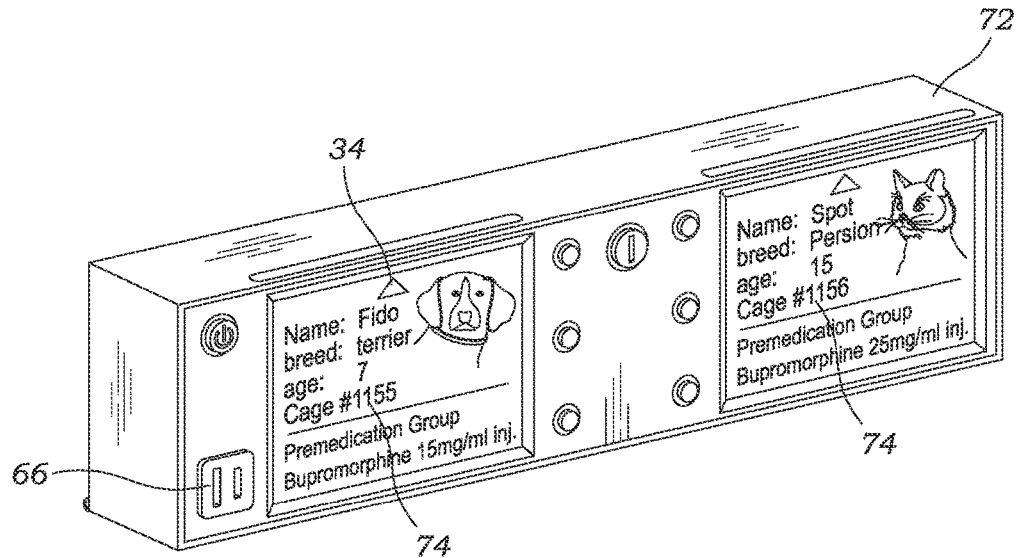
FIG. 5 is a perspective view of a display device from the third embodiment shown in FIG. 4.

FIG. 4 is a perspective view of a third embodiment of a wireless digital treatment and warning system 70. In this embodiment, the system 70 includes a smaller housing 72 that is adapted to be mounted on the face of the cages 20, such as between the top and bottom cages in a horizontal configuration, as shown, or alternatively, between them in a vertical configuration (not shown). FIG. 5 is a perspective view of the system 70 of FIG. 4, illustrating information displaying, in this case including a cage number 74 for identifying the associated cage 20 (shown in FIG. 4).

Figure 6:
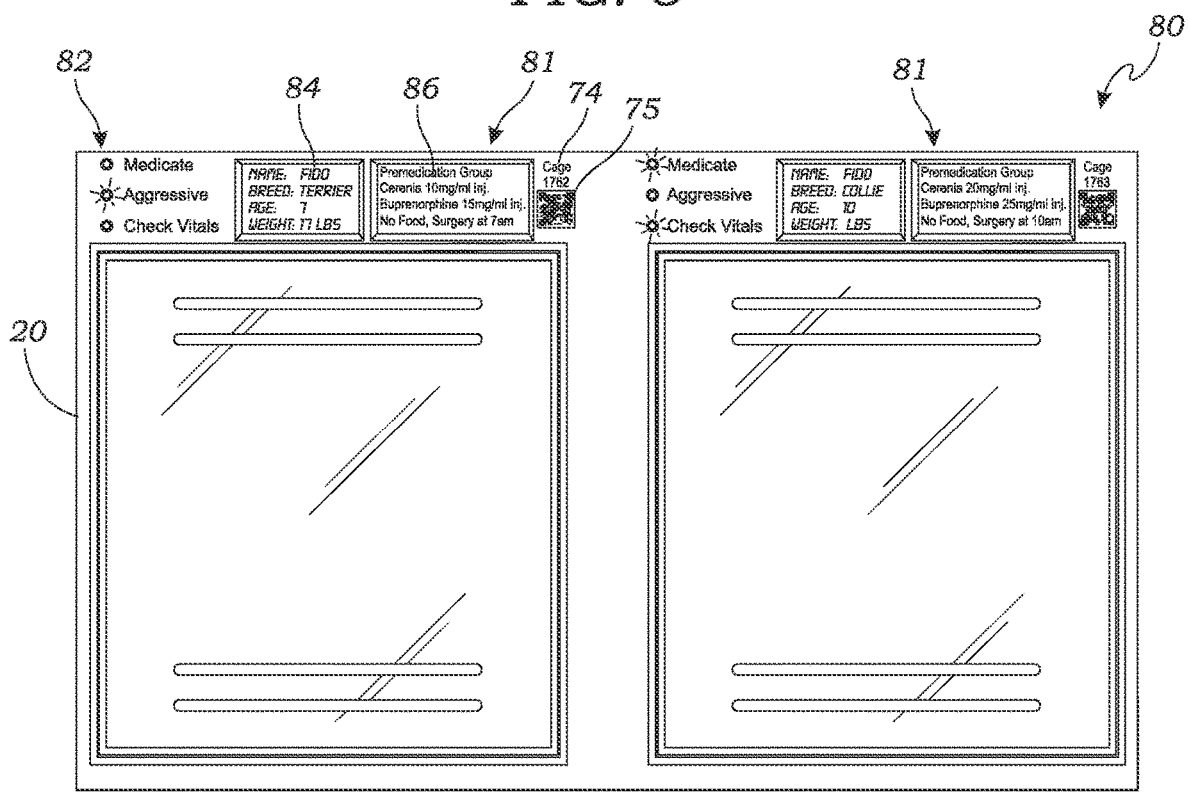
FIG. 6 is a front elevation view of a fourth embodiment of the wireless digital treatment and warning system.

FIG. 6 is a front elevation view of a fourth embodiment of the wireless digital treatment and warning system 80. In this embodiment, the digital display panel 81 is built into the top of the cage 20. This embodiment shows the including of warning lights 82 such as are described above, and two screens for displaying information, a first screen 84 and a second screen 86 (although any number of displays may be used, in any arrangement desired). In this embodiment, the cage code 74 is printed on the cage itself, and there is also a code 75 (e.g., QR code) printed on the cage 20, so that the cage number 75 may be determined automatically by capturing the image of the QR code, and automatically directed to a suitable downloadable app or web page.

Figure 7:
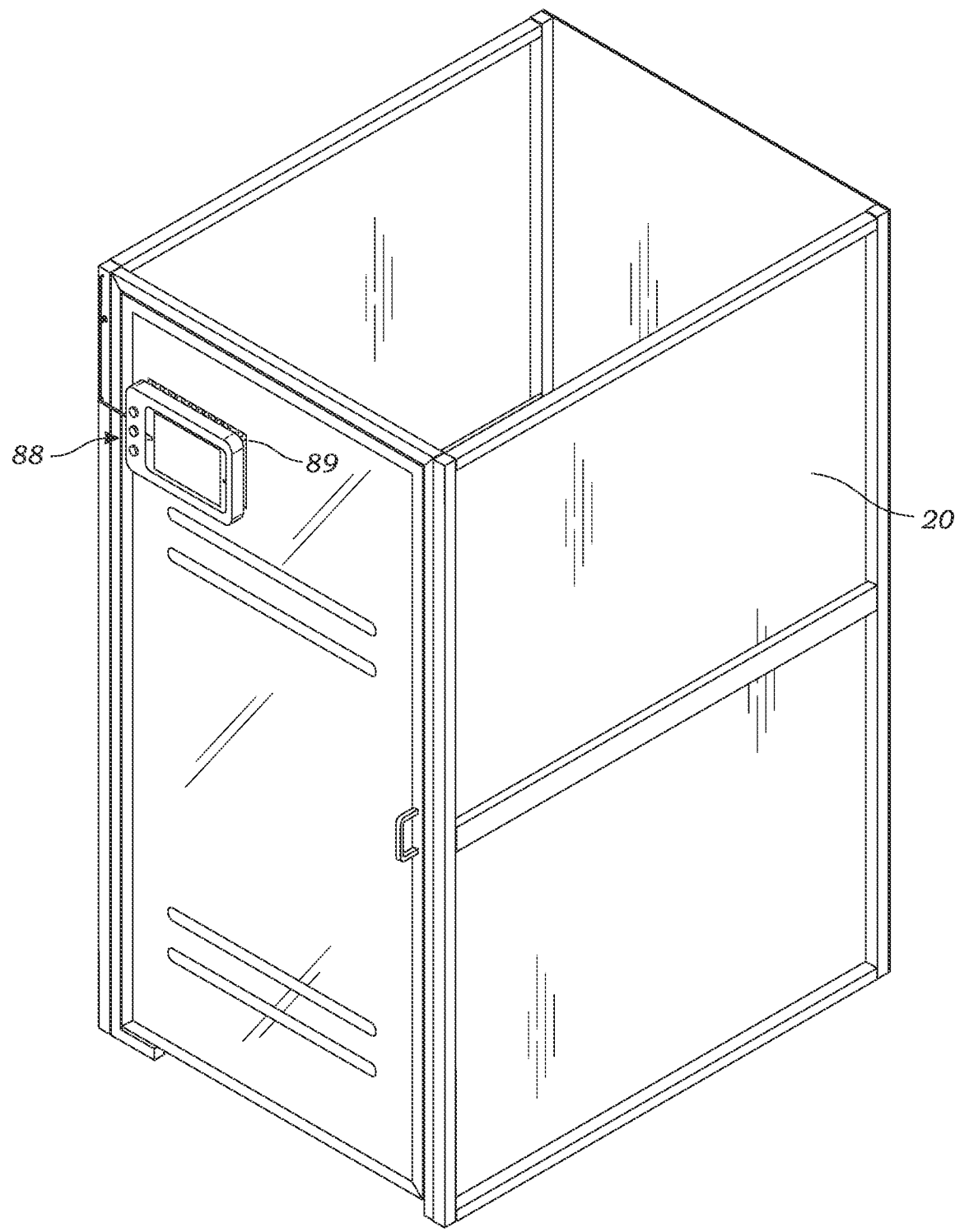
FIG. 7 is a perspective view of a fifth embodiment of a wireless digital treatment and warning system.

FIG. 7 is a perspective view of a fifth embodiment of a wireless digital treatment and warning system 88. In this embodiment, the system 88 is a small display unit which may be mountable (removably or permanently) onto the cage 20 with a fastener 89 (e.g., hooks and loops fasteners, suction cups, adhesives, mechanical fasteners, and/or any other fasteners known in the art).

Figure 8:
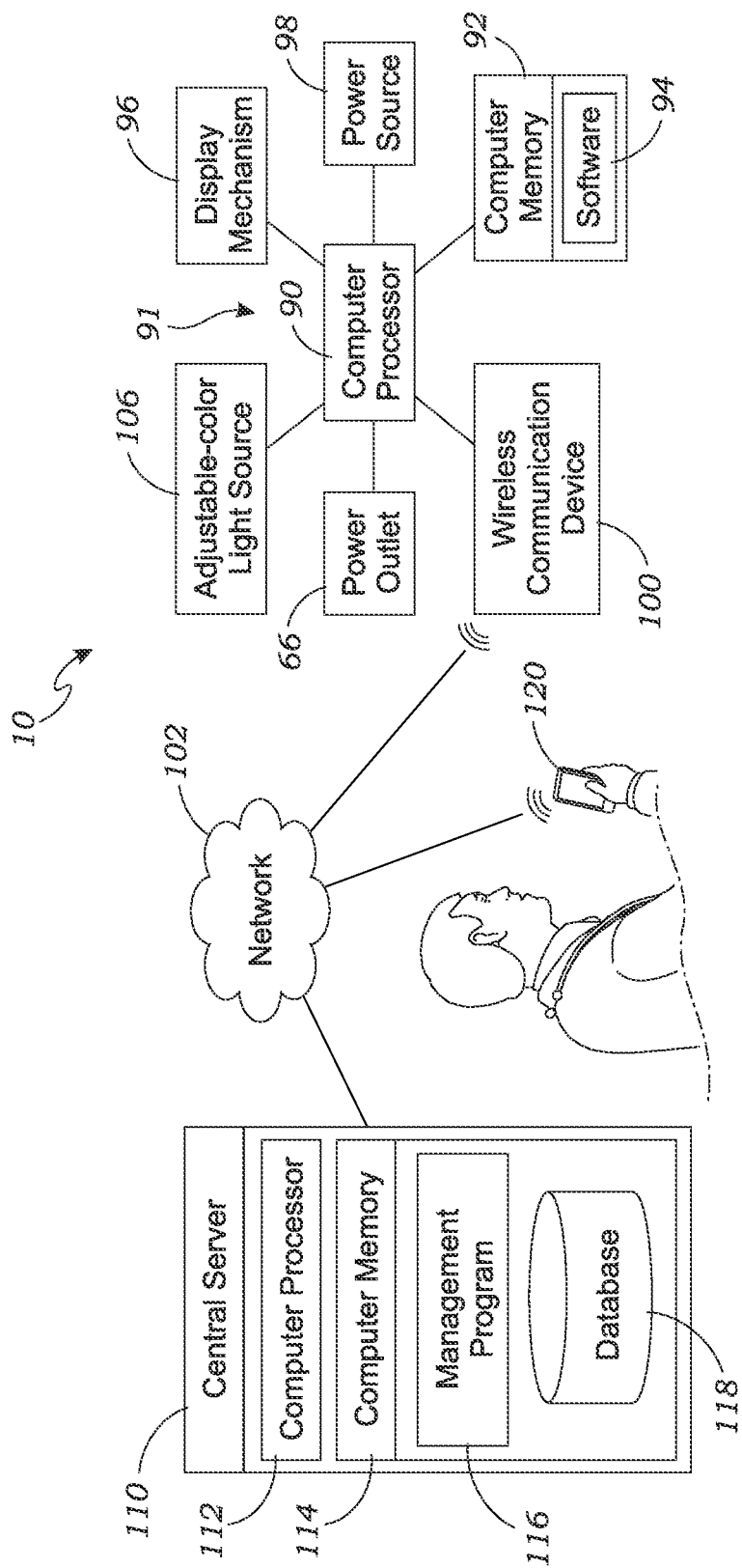
FIG. 8 is a block diagram of internal functional components of the wireless digital treatment and warning system of FIG. 1, and a veterinarian using a smart phone to update the system.

FIG. 8 is a block diagram of internal functional components of the wireless digital treatment and warning system 10 of FIG. 1, and a veterinarian using a smart phone 120 to update the system 10. As shown in FIG. 1, the digital display panel 30 is physically associated with the veterinarian animal cage. As shown in FIG. 8, this digital display panel 30 may include a computer device 91 that may include a computer processor 90, and a computer memory 92 which has operably installed thereupon software 94 which functions as described above. The computer device 91 is operably attached to a display mechanism 96, which may include the display screen 32 or screen discussed above, and may further include the colored warning lights 36, and any other forms of screens, lights, audio, or other multimedia output mechanism known in the art.

The system 10 may be operably attached to a power source 98 (typically an AC outlet in the office, as known in the art). The system may further include a wireless data communication device 100 for communicating with a network 102 (e.g., global computer network, LAN, and/or any other form of communication network known in the art). The system may include the power outlet 66 discussed above. In this embodiment, the system 10 is also operably connected (e.g., wired, wireless, etc.) to an adjustable-color light source 106 such as an LED device, or an LED strip, which is positioned within the animal cage 20 (as shown in FIG. 1). The system 10 functions to adjust the color of the adjustable-color light source 106 to indicate a warning about the aggressiveness of the animal, to indicate that the animal requires medication, and or any other indication known in the art. For example, the adjustable-color light source 106 might illuminate the cage with red to warn that the animal is aggressive or upset, orange to indicate that the animal needs to be administered a drug or receive some form of treatment, blue to indicate he or she does not get food, etc. Obviously, any color scheme may be used, according to the product designer's determinations and instructions.

In this embodiment, the system 10 further includes a central computer 110 having a computer processor 112 and a computer memory 114 which has operably installed thereupon a management program 116 for central administration of the system 10. This enables cage codes to be added, amended, updated, removed, etc. It also enables users (e.g., caregivers, veterinarians, etc.) to input data, enter treatment regimes, etc. It may also be accessible by pet owners for entering data, monitoring their pet and/or his or her treatment. A database 118 may be provided for storing all of this data and making it available to the system 10.

The system 10 may operate autonomously and rely on it's own custom programming, and it may also be linked to existing practice management software systems (e.g., Cornerstone, ExyVet, etc.). When veterinarians or other caregivers enter information into the system 10, not only is the information available at the cage, this information may also be automatically entered into the existing practice management software system, thereby saving time and effort to re-enter the data into a desktop system. This dual system also functions as a backup of the data, so the failure of one system will not result in the loss of the data.

The system 10 also functions to facilitate transfer of information between veterinarians or other caregivers when they are making rounds, coming, going, or a new person is brough in, etc. The transfer typically occurs at the cage, where the veterinarian or other caregiver discusses the case with the new person. The system 10 enables an easy transfer, the data is all there on the screen, and no notes need to be transferred.

Figure 9:
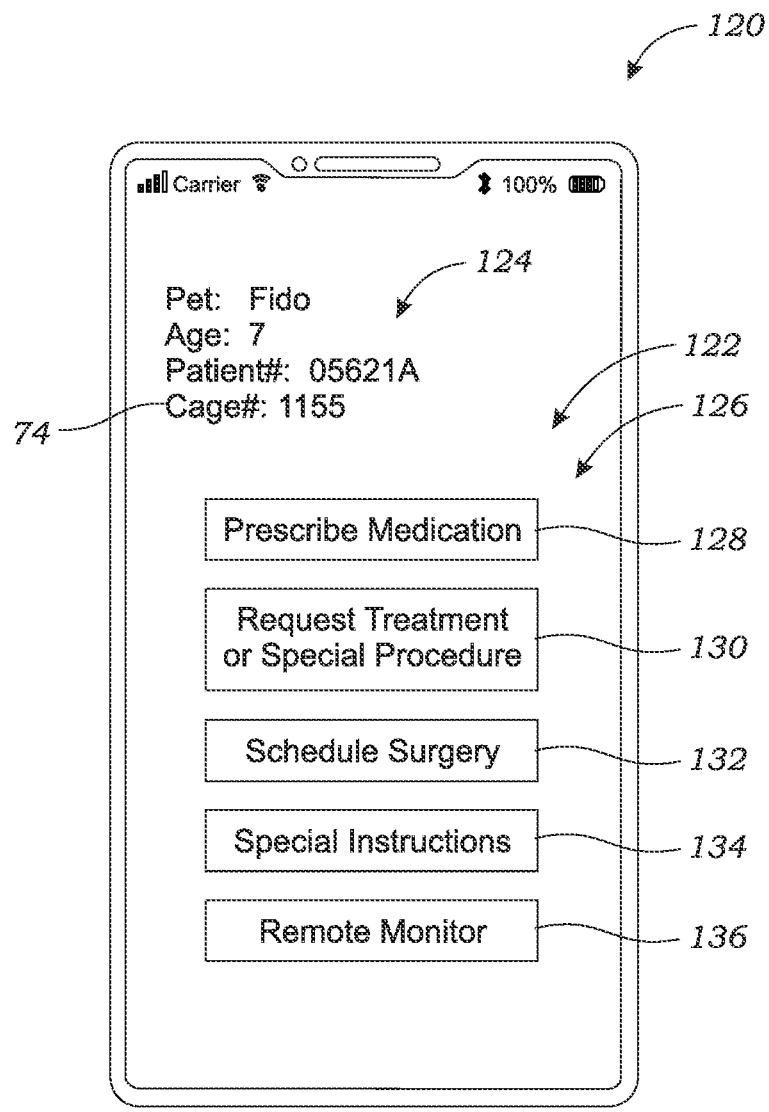
FIG. 9 is a front elevation view of a smart phone shown in FIG. 8 being used to update the system.

FIG. 9 is a front elevation view of the smart phone 120 shown in FIG. 8 being used to update the operation of the system 10 of FIG. 1. As shown in FIG. 9, the smart phone 120 (the term "smart phone" in this context is defined to include any form of computer device, typically but not necessarily portable, which may be used for entry of data and control of the system 10, including phones, tablets, laptops, etc.).

As shown in FIG. 9, the smart phone 120 includes a display 122 for displaying animal information 124 (including cage number 74 where the animal is kept), as well as functional options 126 for controlling the system 10. In this case, this includes a prescribe medication function 128 for prescribing medication and course of treatment, a request function 130 for requesting a treatment or special procedure, a schedule surgery function 132, a special instructions function 134, and a remote monitor function 136 which may be used to remotely observe the animal, typically be streaming video from a camera (not shown) located near the cage 20. This functionality may also be made accessible to the public, for purposes of pet adoption, etc. While this embodiment is shown to illustrate one alternative for this display 122, those skilled in the art may devise a wide range of options which should be considered within the scope of the present invention.

The title of the present application, and the claims presented, do not limit what may be claimed in the future, based upon and supported by the present application. Furthermore, any features shown in any of the drawings may be combined with any features from any other drawings to form an invention which may be claimed.

As used in this application, the words "a," "an," and "one" are defined to include one or more of the referenced item unless specifically stated otherwise. The terms "approximately" and "about" are defined to mean+/−10%, unless otherwise stated. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application. While the invention has been described with reference to at least one particular embodiment, it is to be clearly understood that the invention is not limited to these embodiments, but rather the scope of the invention is defined by claims made to the invention.

We claim:

1. A wireless digital treatment and warning system for displaying information to a veterinarian about animals, the wireless digital treatment and warning system comprising:
a veterinarian animal cage having a cage body and a hinged door that allows access to the cage body;
a tablet computer having a computer processor, a computer memory, a wireless data communication device, and a display screen, the tablet being operably mounted on the veterinarian animal cage;
a digital display panel mounted on the veterinarian animal cage, upon which the tablet computer is mounted;
a cuboid housing upon which the digital display panel is pivotally mounted, the cuboid housing being physically mounted on the veterinarian animal cage, and the tablet computer is slidably mounted on retainer mechanisms of the digital display panel;

a central server having a computer processor and a computer memory, the central server being operably connected with the tablet computer, the central server having a management program and a database installed in the computer memory for storing the information about the animals, and for transmitting information related to the animal housed in the veterinarian animal cage to the tablet computer, so that the information may be visually outputted on the display screen; and wherein the tablet computer receives input from the veterinarian regarding a course of treatment provided to the animal in the veterinarian animal cage, and transmits the course of treatment to the central server where it is stored in the database of the central server.

2. The wireless digital treatment and warning system of claim 1, further comprising one or more colored warning LEDs mounted on the digital display panel, apart from the tablet computer, which are operably connected to the tablet computer to provide a visual warning alert that it is presently time to medicate, time to feed, not medicate/feed, when an animal is aggressive, or indicate a problem in vital signs of the animal.

3. The wireless digital treatment and warning system of claim 1, wherein the computer device is operably connected to an adjustable-color light source positioned within the animal cage, and the computer device functions to adjust the color of the adjustable-color light source from white to another color to indicate a warning about the aggressiveness of the animal.

4. The wireless digital treatment and warning system of claim 1, wherein the computer device is operably connected to an adjustable-color light source positioned within the animal cage, and the computer device functions to adjust the color of the adjustable-color light source from white to another color to indicate that the animal requires medication.

5. A wireless digital treatment and warning system for displaying information about animals, the wireless digital treatment and warning system comprising:
   two veterinarian animal cages, a top cage and a bottom cage, each having a cage body and a hinged door that allows access to the cage body;
   a cuboid housing having a digital display panel that is pivotally mounted to the cuboid housing, the cuboid housing being positioned between the top and bottom cages, so that the top cage is supported upon the cuboid housing;
   the digital display panel having retainer mechanisms for receiving a pair of tablet computers, each of the tablet computers having a computer processor, a computer memory, a wireless data communication device, and a display screen, the tablet computers being mounted on the digital display panel so that the display screen of the tablet computers are visible through the digital display channel;
   wherein of each of the tablet computer is associated with one of the top or bottom cages, so that the information about the animals displayed on the display screens is associated with one of the veterinarian animal cages;
   a central server having a computer processor and a computer memory, the central server being operably connected with the pair of tablet computers, the central server having a management program and a database installed in the computer memory for storing the information about the animals, and for transmitting information related to the animal and a course of treatment for the animal housed in the veterinarian animal cage, so that the information may be visually outputted on the display screen; and
   wherein each of the tablet computers is further capable of receiving input from the veterinarian regarding the course of treatment provided to the animal in one of the veterinarian animal cage, so that this information and course of treatment may be received by the central server and stored in the database.

6. The wireless digital treatment and warning system of claim 5, further comprising colored warning LEDs mounted on the digital display panel adjacent the retainer mechanisms, the colored warning LEDs being operably connected to the tablet computer to provide a visual warning alert when the animal requires attention.

7. The wireless digital treatment and warning system of claim 5, wherein the tablet computer is operably connected to an adjustable-color light source positioned within the veterinarian animal cage, so that the colors of the adjustable-color light source is controlled by the tablet computer to change the color of the adjustable-color light source from white to another color to indicate a warning about the aggressiveness of the animal.

8. A wireless digital treatment and warning system for displaying information about animals, the wireless digital treatment and warning system comprising:
   two veterinarian animal cages, a top cage and a bottom cage, each having a cage body and a hinged door that allows access to the cage body;
   a cuboid housing having a digital display panel that is pivotally mounted to the cuboid housing, the cuboid housing abutting at least one of the top and bottom cages;
   the digital display panel having retainer mechanisms for receiving a pair of tablet computers, each of the tablet computers having a computer processor, a computer memory, a wireless data communication device, and a display screen, the tablet computers being mounted on the digital display panel so that the display screen of the tablet computers are visible through the digital display channel;
   wherein of each of the tablet computer is associated with one of the top or bottom cages, so that the information about the animals displayed on the display screens is associated with one of the veterinarian animal cages;
   a central server having a computer processor and a computer memory, the central server being operably connected with the pair of tablet computers, the central server having a management program and a database installed in the computer memory, wherein the management program performs the following steps:
      storing the information about the animals that are housed in the veterinarian animal cages;
      associating, in the database, the stored information for each of the animals with the tablet computer that is associated with the veterinarian animal cage in which that animal is housed;
      displaying on the display screen of the associated tablet computer at least some of the information in the database regarding that animal;
      receiving input from the veterinarian via one of the tablet computers regarding a course of treatment provided to the animal in one of the veterinarian animal cages;
      transmitting the course of treatment to the central server; and receiving the course of treatment by the central server and storing the course of treatment in the database associated with the associated animal.

* * * * *